United States Patent [19]

Cornyn, Jr. et al.

[11] Patent Number: 4,484,081
[45] Date of Patent: Nov. 20, 1984

[54] DEFECT ANALYSIS SYSTEM

[75] Inventors: William S. Cornyn, Jr.; John S. Barrett, both of Rancho Palos Verdes; Donald C. Brabston, Jr., Sherman Oaks; Peter C. Camana, Los Alamitos; James M. McAferty, Mission Viejo; Steven P. Nelson, Harbor City; Stuart T. Schy, Culver City, all of Calif.

[73] Assignee: TRW Inc., Redondo Beach, Calif.

[21] Appl. No.: 592,734

[22] Filed: Mar. 22, 1984

Related U.S. Application Data

[63] Continuation of Ser. No. 188,651, Sep. 19, 1980, abandoned.

[51] Int. Cl.³ ............................................. G01N 21/88
[52] U.S. Cl. ..................................... 250/563; 358/106; 364/507
[58] Field of Search ............... 250/562, 563, 572, 578; 358/101, 106, 107; 356/237, 238, 430, 394; 364/507, 506, 552, 554, 576, 577, 551

[56] References Cited

U.S. PATENT DOCUMENTS

| | | | |
|---|---|---|---|
| 3,694,658 | 9/1972 | Watson et al. | 250/227 |
| 3,729,619 | 4/1973 | Laycak et al. | 250/219 |
| 3,795,452 | 3/1974 | Bourdelais et al. | 356/237 |
| 3,964,830 | 6/1976 | Ikeda et al. | 250/572 |
| 4,002,823 | 1/1977 | Van Oosterhout | 250/223 B |
| 4,183,013 | 1/1980 | Agrawala et al. | 382/9 |

FOREIGN PATENT DOCUMENTS

| | | |
|---|---|---|
| 2009395 | 6/1979 | United Kingdom . |
| 2057675 | 1/1981 | United Kingdom . |
| 2064762 | 6/1981 | United Kingdom . |

*Primary Examiner*—David C. Nelms

[57] ABSTRACT

Disclosed is an apparatus, and a related method, for the automatic detection of defects in manufactured parts, such as turbine blades and the like. The apparatus includes a video camera, a thresholding module to provide a binary image of a frame of video data, a region growing module to define anomalous regions by associating contiguous picture elements indicative of surface anomalies on the part, and defect analysis modules for determining if a rejectable defect exists, based on a comparison between statistics with respect to the anomalous regions and predetermined rejection criteria. Rejection may be based on region size, region shape, or region position and orientation with respect to neighboring regions. Thus, a region may be rejected if it is nearly collinear with another region, even though neither region may itself be characterized as a rejectable region.

24 Claims, 11 Drawing Figures

DEFECT ANALYSIS SYSTEM

This is a continuation of U.S. patent application Ser. No. 188,651 filed Sept. 19, 1980, now abandoned.

BACKGROUND OF THE INVENTION

This invention relates generally to defect detection systems, and, more particularly, to apparatus and a related method for detecting defects in manufactured parts, such as turbine blades, automobile engine parts, and other components that can fail under mechanical stress because of some inherent structural defect. Turbine blades in jet engines, for example, are subjected to substantial mechanical stresses under demanding conditions of temperature and pressure. Under these conditions, a defective part can fail without warning, often with potentially dangerous consequences. Defects in metal parts fabricated by casting and other processes are usually detectable as anomalies in the surface of the part. Defects caused by metal fatigue may also show up as surface anomalies. Surface anomalies may be cracks or pits, but they are often so small as to be invisible to the human eye under normal lighting conditions.

A number of processes have been developed to aid in the visual inspection of parts for surface defects. Some of these are known by the proprietary names Magnaflux, Magnaglo and Zyglo. Basically each of these processes requires that the part be first coated with a material that improves the contrast between the possible defects and the remaining or background area of the part. The part under inspection is illuminated, usually with ultraviolet light, which produces visible radiation when it impinges on the coating material, and an operator inspects it thoroughly for defects. Even with the use of these defect enhancement techniques such as these, there is still a significant change that defects will go undetected, mainly as a result of operator inattention and fatigue. To ensure practically complete freedom from defects, a batch of parts may have to be inspected several times over.

In some defect detection schemes of the prior art, a video camera is used to convert the defect images to analog electrical signals for display on a screen, and the images may then be enhanced by means of electronic image processing techniques. However, a decision as to whether the part should be rejected or not is still made as a result of inspection of the enhanced image by an operator.

It will be apparent from the foregoing that there has been a significant need for an improved defect detection system which relieves the operator of the burden of deciding whether a surface anomaly constitutes a rejectable defect. The present invention fulfills this need.

SUMMARY OF THE INVENTION

The present invention, in its broadest sense, resides in a system for analyzing an image of an object by generating region-related image data representative of the geometries of distinctive regions in the image, and comparing this region-related image data with preselected geometric parameters. Briefly, and in general terms, the system of the invention includes imaging means to provide signals representative of discrete picture elements in the image, means for selecting from the signals those corresponding to picture elements that are distinct from other picture elements, means for processing the selected signals to define the geometry of one or more regions of contiguous picture elements that are distinct from other picture elements, and means for comparing the geometry of the one or more regions with predetermined region geometry parameters, to analyze each region with respect to such parameters and to provide an output indicating how the region compares with the parameters.

More specifically, the present invention resides in an automatic defect analysis system, and a related method for its operation, by means of which possible defect regions are detected and categorized with respect to their size, shape and orientation, and a decision is made as to whether each such defect region constitutes a rejectable defect based on predetermined rejection criteria. The defect analysis system of the invention includes video camera means for obtaining electrical signals representative of an image frame presented for analysis, thresholding means for generating from the image frame a set of electrical signals indicative of anomalous picture elements that are optically distinct from other picture elements, and region growing means for associating contiguous picture elements to define continuous regions of anomalous picture elements. In addition the system includes region statistics generation means for generating statistics relative to the size, shape, position and orientation of the regions, and region analysis means for comparing the region statistics with predetermined rejection parameters to determine whether a rejectable defect is present.

In accordance with a more specific aspect of the invention the thresholding means includes means for computing a histogram of the image frame to define the relationship between image intensity and numbers of picture elements. The system further includes means for calculating a threshold level from the histogram information, such that all elements above the threshold level are considered to be anomalous, and image thresholding means for producing binary images of the anomalous areas.

The region growing means of the invention associates contiguous anomalous picture elements to form regions corresponding to anomalous portions of the original image. In particular, each anomalous picture element is tagged with a region number, and regions are combined when it is subsequently discovered that they are part of one continuous region, rather than two discrete regions. In addition, regions whose total area is below a minimum threshold level are discarded as being of no consequence in the defect analysis.

The region statistics generation means includes means for accumulating statistics relative to the co-ordinates of picture elements in each region, and for deriving further statistics with respect to the location, shape, orientation and size of each region. More particularly, since regions constituting defects are often approximately elliptical in shape, means are provided for determining the lengths of major and minor axes of an ellipse having the same area as the region, and for determining the orientation of the ellipse with respect to a reference axis. In addition, the total area of the region and its center of area are recorded.

Many different rejection criteria can be formulated, and the specific criteria utilized will depend on the geometry of the part under analysis and on the specifications of the manufacturer and purchaser of the parts. One important criterion, however, is the magnitude of the total area of the region. If the total area exceeds a preselected limit, the region can be considered to constitute a rejectable defect. Even if the region is below the preselected limit, it may still constitute a rejectable defect if its length-to-width ratio exceeds another preselected limit. In this regard, long, narrow surface defects, which may be cracks or fissures, are more likely to constitute rejectable defects than are defects that are more nearly circular shape.

Although two or more regions may not constitute rejectable defects when considered separately, they may, when considered together, represent surface portions of a crack extending below the surface of the part under examination. In accordance with another important aspect of the invention, means are provided for determining whether two or more regions can be considered to constitute a single defect based upon their relative proximity and their orientation. More specifically, two regions will be considered connected or connectable if their centers are within a specified relative distance range and if their major axes are both parallel within certain limits and are aligned with a straight line connecting the centers of the regions, again within certain angular limits. Only if all these tests are met will the regions be considered to be connected or connectable. The criterion for rejectability may be, for example, that only two such regions are connectable in this manner, or that three or more regions are connectable to constitute a single defect.

In terms of a novel method, the invention includes the steps of obtaining electrical signals representative of the image frame presented for analysis, transforming these signals into a set of binary electrical signals indicative of anomalous picture elements that are optically distinct from the other picture elements, associating contiguous picture elements to form anomalous regions, generating statistics relative to physical characteristics of the regions, such as size, shape, position and orientation, and comparing the region statistics with predetermined rejection parameters to determine whether a rejectable defect is present. More specifically, as it applies to thresholding, the method of the invention includes generating a histogram of the image frame, calculating an optimum threshold from the histogram, and generating a binary image from the threshold and the original image frame.

It will be appreciated from the foregoing that the present invention represents a significant advance in the field of defect detection systems. In particular, the invention provides a novel technique for rejecting or accepting parts with possible defects, based upon the size, shape, relative position, and orientation of regions representing possible defects. Other aspects and advantages of the invention will become apparent from the following more detailed description taken in conjunction with the accompanying drawings.

DESCRIPTION OF THE PREFERRED EMBODIMENT

Overview

Figure 1:
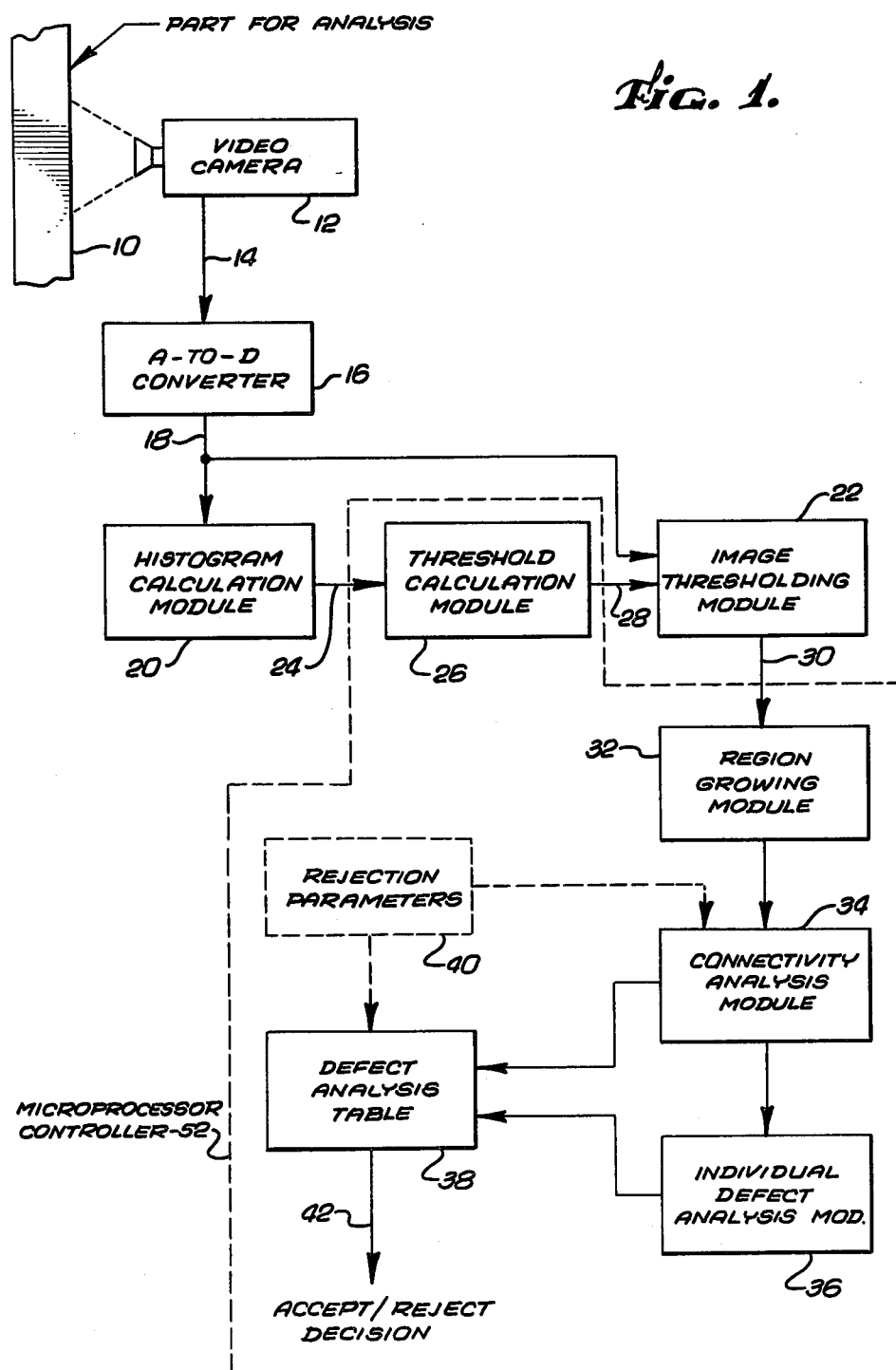
FIG. 1 is a simplified block diagram of the system of the invention.

As shown in the drawings for purposes of illustration, the present invention is concerned with the detection of defects, such as might be caused during fabrication or by fatigue stresses, in manufactured parts and components. Such defects are usually evidenced by surface cracks or fissures, and, prior to this invention, have been detected only by inspection by an operator. Typically, a part under inspection is first treated or coated with a suitable material to enhance the contrast between the defects and background areas, and then exposed to ultraviolet radiation. The material penetrates the defects, and produces visible light when exposed to the ultraviolet radiation. In some such inspection systems, video cameras are used to enlarge or otherwise enhance the image of the part, but rejection is still based on the results of a visual inspection by the operator.

In accordance with the present invention, an image of anomalous surface regions is obtained from a video camera, and region statistics with respect to the size, position, shape, and orientation of the regions are generated and compared with predetermined rejection parameters in order to determine if one or more of the regions constitutes a rejectable defect. Once the rejection parameters have been established for a particular part being examined, based on experience and on desired manufacturing standards, defect detection can proceed automatically without operator inspection of the part.

As shown on FIG. 1, a part being analyzed for defects, indicated by reference numeral 10, is scanned by a video camera 12. It is assumed that the part 10 has been appropriately treated and is illuminated by an ultraviolet, or other appropriate light source, in accordance with one of the conventional surface defect analysis techniques, such as Magnaflux, Magnaglo, or Zyglo. These processes form no part of the present invention, of course, but are representative of conventional techniques by means of which a suitable degree of contrast may be obtained between a surface anomaly and its background. The coating employed in the processes penetrates the defects, and emits visible light when irradiated with an appropriate source, usually in the ultraviolet range. It will become apparent as this description proceeds that the invention would be equally applicable to systems incorporating x-ray analysis, wherein an x-ray image is converted to a video image for subsequent processing in accordance with the invention.

The video camera 12 and its associated lens system (not shown) should be designated and selected to be extremely sensitive to the frequencies radiated from defects in the part being examined. In particular, the present camera is a Cohu Model 4410 silicon-intensified-target camera having a very high sensitivity. Unfortunately, such cameras are also sensitive to radiation in the infrared region, and an appropriate infrared filter is needed. In the Zyglo process for example, the coating used is a phosphor that produces a yellow-green component having a wavelength near 540 nanometers (nm) when irradiated with ultraviolet light in the 365 nm region. So that anomalous regions can be viewed with suitable contrast, narrow passband filter is employed to pass only the 540 nm component to the video camera 12.

As also shown in FIG. 1, the video camera 12 generates a video output signal on line 14, which is connected to an analog-to-digital converter 16, to provide sampled digital outputs on output line 18. The digital outputs on line 18 are transmitted to a histogram calculation module 20 and to an image thresholding module 22, the function of both of these modules being explained below. The histogram calculation module 20 provides histogram information over line 24 to a threshold calculation module 26, the output of which, on line 28, is transmitted to the image thresholding module 22. The output of the thresholding module 22, on line 30, is a set of binary signals indicative of anomalous picture elements. These are analyzed by a region growing module 32, where the individual picture elements are associated with each other to form binary signals indicative of continuous anomalous regions.

The remaining elements of the system are a connectivity analysis module 34, an individual defect analysis module 36, and a defect analysis table 38. In the connectivity analysis module 34 and the individual defect analysis module 36, the regions derived from the region growing module 32 are analyzed to produce statistics with respect to their size, position, shape, and orientation, these statistics being stored in the defect analysis table 38. A set of rejection parameters, indicated by the block 40 shown in broken lines, are used to make comparisons with the region statistics to obtain a decision signal, on line 42, indicating whether the part under examination should be accepted or rejected.

The sampling rate of the analog-to-digital converter 16 in the illustrative embodiment is such that 512 discrete samples are obtained for each line of video data. These signal samples appear on line 18 as a six-bit digital stream of data, representing the detected light intensity of each picture element in a frame of video data, measured on a six-bit gray scale having possible values from zero to sixty-three. In the illustrative embodiment, the video camera 12 operates in a conventional interlaced fashion, since the video signals from the camera may also be used to operate a monitor (not shown) used for confirming the results by visual inspection. In interlacing, odd numbered lines are scanned first, this being referred to as the odd field, and then the even numbered lines are scanned to form the even field. Although interlacing is not an essential part of the invention, it facilitates display of the video image. However, its use in the disclosed embodiment necessitates somewhat more complex circuitry than would be necessary without interfacing.

Thresholding in General

Before the images of possible defect areas can be analyzed in any meaningful fashion, the grayscale images are first converted to binary (black and white) images for ease of further manipulation. One way of doing this would be to designate a particular intensity level as a threshold and to designate all picture elements having intensities equal to or above that level as white elements, and all those below the level as black elements. However, this technique does not provide consistently good results, prinicipally because of variations in optical characteristics in the parts being examined, and also because of gradual drift in the performance characteristics of the electrical components in the system.

Figures 2, 3:
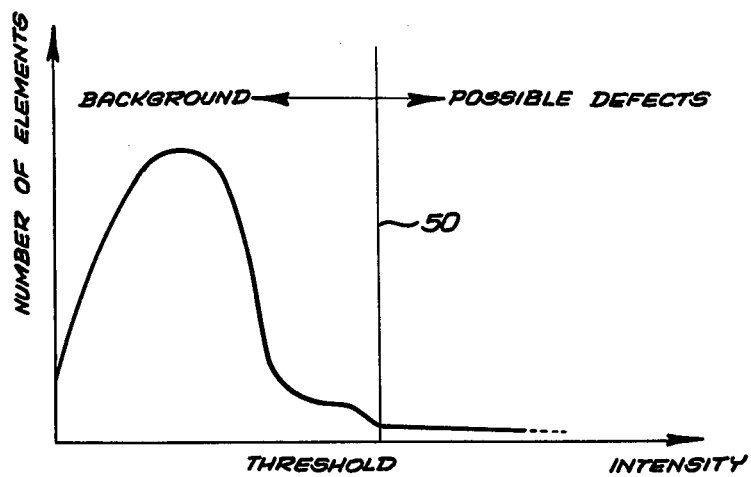
FIG. 2 is a graphical representation of a histogram distribution showing the relationship between numbers of picture elements and their intensity.
FIG. 3 is a graphical and fragmentary representation showing a picture frame of binary picture elements divided into square blocks of 64 elements each.

In accordance with one aspect of the invention, a histogram is first prepared in the histogram calculation module 20, and a threshold level is determined for each new frame of information by the threshold calculation module 26. The histogram is a set of accumulated counts of picture elements, one count for each of the sixty-four brightness levels. Thus, in the histogram calculation module 20, sixty-four counts are accumulated, one for each of the gray-scale levels from 0 to 63. The results of the histogram calculations are shown graphically in FIG. 2. Typically, the majority of the elements have an intensity falling at the low end of the gray scale, there usually being a distinct peak formed part-way along the gray scale. Those elements having intensities falling at the upper end of the gray scale are indicative of possible surface anomalies in the part being examined. It is the function of the threshold calculation module 26 to select a threshold line, indicated at 50 in FIG. 2. Picture elements with intensities equal to or above the threshold will be designated as anomalous elements, and those below the threshold as background elements. The threshold calculation module 26 examines the histogram counts and selects the position of the threshold line 50 in accordance with a predetermined formula, as discussed below, by way of example, in relation to FIG. 6a. Then, in the image thresholding module 22, each picture element intensity is compared with the threshold level to obtain a binary indication of the element's intensity with respect to the threshold. Thus, the image thresholding module produces a binary image of the frame, shown by way of example in FIG. 3, where zeros represent picture elements with intensities falling below the threshold and ones indicate anomalous picture elements with intensities falling on or above the threshold.

Although the histogram calculation module 20 threshold calculation module 26 and image thresholding module 22 can be implemented in a variety of ways, including hard-wired electronic components, special purpose microcomputers, or a programmed general purpose computer, as a practical matter computation times are undesirably long if programmed computers or microprocessors are used for all of the modules. In the disclosed embodiment, in the histogram calculation module 20 and the image thresholding module 22 are both implemented in hard-wired form, while the threshold calculation module 26 and the remaining modules of the system are implemented in microprocessor form, as indicated by the broken lines 52 in FIG. 1. In this manner, a complete frame of data can be analyzed for defects in less than a second. The hard-wired modules 20 and 22 are shown in detail in FIGS. 4 and 5, respectively, and will now be described in detail before turning to a discussion of the region growing module 32 and the remaining defect analysis modules.

Histogram Calculation Module

Figure 4:
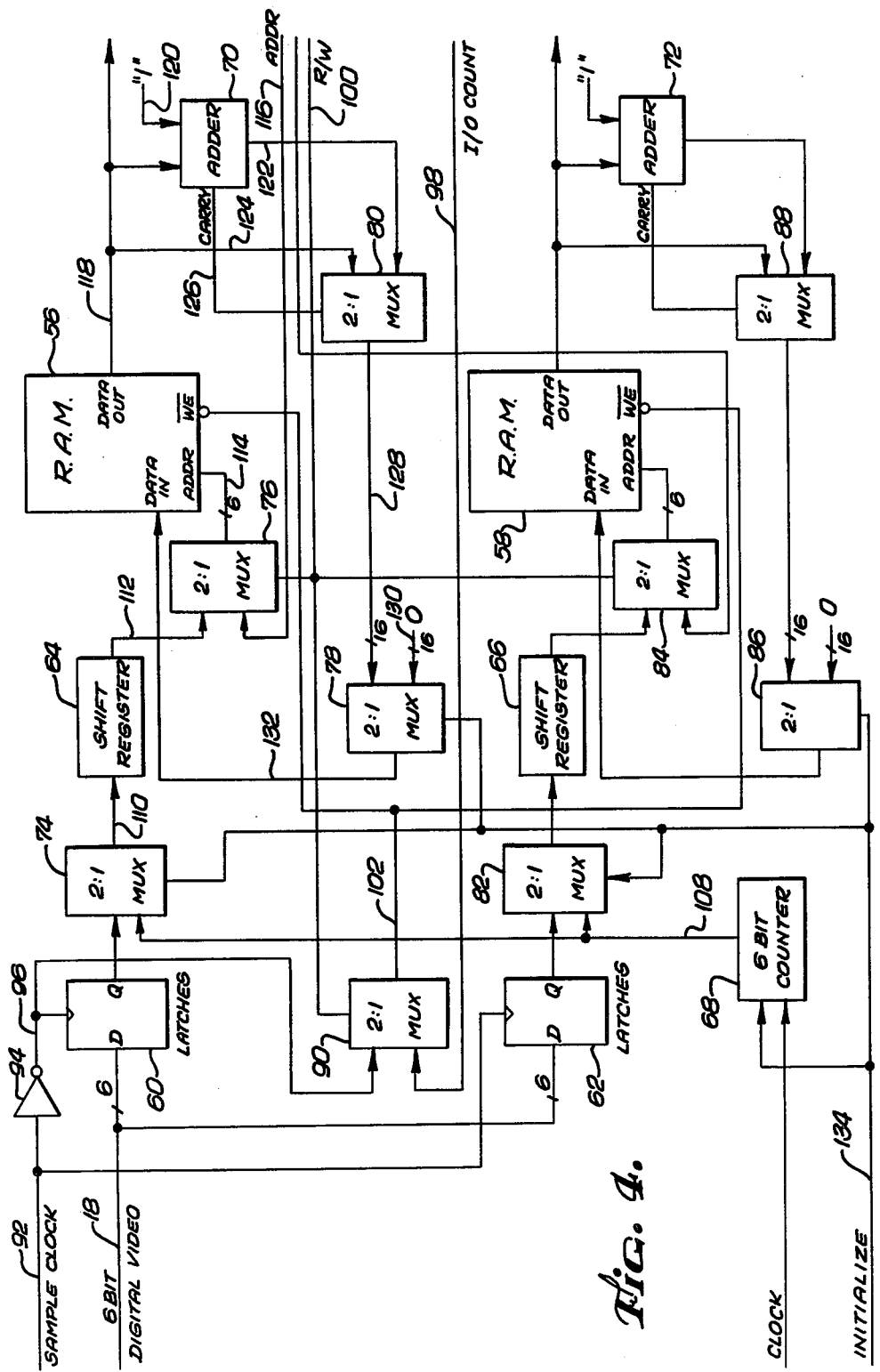
FIG. 4 is a schematic diagram of the histogram calculation module of FIG. 1.

As shown in FIG. 4, the histogram calculation module receives a stream of six-bit digital video signals over line 18 from the analog-to-digital converter 16 (FIG. 1) and includes two random access memories (RAM) 56 and 58 in which are accumulated a set of counts indicative of the number of picture elements in the frame for each gray-scale level. As will shortly become apparent, two memories are used in order to increase the speed at which the computation proceeds. When the computation is ended, the contents of corresponding addresses in the two memories are added together to produce the total histogram counts. Other elements in the histogram calculation module 20 include two six-bit latches 60 and 62, two shift registers 64 and 66, a six-bit counter 68, two adders 70 and 72 and nine 2-to-1 multiplexers, indicated at 74, 76, 78, 80, 82, 84, 86, 88, and 90. The multiplexers function as multipole switches having two multi-bit input lines and one multi-bit output line, together with a control signal line, the state of which determines which of the input lines will be connected to the output line.

The six-bit digital video signal on line 18 is connected to the data inputs of the latches 60 and 62, and clocking signals to the latches are provided over a sample clock signal line 92, which is connected directly to the clocking terminals of latches 62 and is connected through an inverter 94 and over line 96 to the clocking terminal of the latches 60. Line 96 is also connected as one input to multiplexer 90, the other input being obtained over line 98 and used to supply an input-output control signal supplied to the histogram calculation module. A read/write signal on line 100 to the module is connected as a control signal to the multiplexer 90, and determines whether the inverted sample clock signal on 96 or the input-output control signal on line 98 is obtained on an output line 102 from multiplexer 90. The output line 102 is connected to inverse write-enable terminals of the memory units 56 and 58, and selects from the reading and writing functions of the memories.

The sample clock signal on line 92 clocks alternate six-bit samples into the latches 60, for example all the odd-numbered samples, and clocks the other samples, for example the even-numbered samples, into the latches 62. Processing of the odd-numbered and even-numbered samples then proceeds essentially in parallel. Accordingly, only one set of these parallel processing elements need be described in detail.

The outputs of the latches 60 are connected over line 106 as one input to multiplexer 74, the other input being provided over line 108 from the 6-bit counter 68. The output of multiplexer 74, on line 110, is transmitted to the shift register 64, and thence over line 112 as one input to multiplexer 76. The function of shift registers 64 and 66 is to synchronize operations on the memory units 56 and 58. The output of multiplexer 76 is, in turn, transmitted over line 114 to the address terminals of memory 56. The other input to multiplexer 76 is provided on line 116, and is an address of a memory location from which data is to be read by the microprocessor 52 (FIG. 1). The signal on the control line to multiplexer 76 is derived from line 100, bearing the read/write signal from the microprocessor. When control line 100 indicates the read mode, the multiplexer selects an address supplied over line 116. When control line 100 indicates the write mode, the address supplied to the memory on line 114 is derived from the shift register 64 over line 112. Basically, the data in the latches 60 are used to generate an address for writing into the memory unit 56. The memory 56 is initially filled with all zeros, in a manner to be described, then each memory location is employed to store a count of the number of times that that location is addressed by the incoming data.

The count accumulation is effected by means of the adder 70, which receives data output from the memory unit 56, over line 118, and adds one to the count as indicated by adder input 120, to produce an incremented output on line 122 for transmission as one input to multiplexer 80. The other input to the multiplexer 80, on line 124, is derived directly from the data output line 118, and is selected as an input only when an adder overflow is indicated by a carry signal on line 126, used as the control line for the multiplexer 80. A carry signal will be generated only when the count in the adder 70 reaches the full capacity of the adder. Thus, the output of multiplexer 80, on line 128, is the incremented data output, or the unincremented output if the value of the count has reached its upper limit. This 16-bit accumulated count on line 128 is provided as one input to multiplexer 78, the other input of which, on line 130, is an all-zero input used only for initialization purposes. The output of multiplexer 78, on line 132, is provided to the data input terminals of the memory 56.

An initialize signal on line 134 is used to reset the six-bit counter 68, to select the zero inputs of multiplexers 78 and 86, and to select the address inputs from the counter 68 for the multiplexers 74 and 82. Thus, when the initialize signal is present on line 134, a sequence of addresses is provided by the six-bit counter, transmitted through the multiplexers 74 and 82 and the shift registers 64 and 84, and finally applied to the address inputs of the memory units 56 and 58. During the time that the address input terminals are being cycled through their range of addresses, the data provided through multiplexers 78 and 86 and supplied to the data input terminals of the memories 56 and 58 are all zeros. In this manner, the memory units 56 and 58 are completely zeroed prior to calculation of a histogram. When the initialize signal is removed from line 134, data from the latches 60 and 62 are provided to the multiplexers 74 and 82, and are used to generate addresses for application to the memory units 56 and 58. Each time a storage location is addressed in the memory 56, its contents are output on line 118, incremented in adder 70, fed back through multiplexers 80 and 78, and stored again in the memory 56.

The reading and writing cycles of the memory 56 are controlled basically from the inverted sample clock signal 96, which is fed through the multiplexer 90 and thence over line 102 to the write-enable terminals of the memory units 56 and 58. When the read/write signal on line 100 is in the write condition, multiplexer 90 derives its input from the input-output control signal on line 98, rather than from the inverted sample clock on line 96, so that the microprocessor 52 can access the memory units 56 and 58 for reading purposes.

Threshold Calculation Module

After a complete frame of video information has been analyzed in this manner, the memories 56 and 58 will contain counts equivalent to the numbers of times that particular data values occur in the picture elements making up the frame. Thus, for example, memory address #0 in memory units 56 and 58 will contain the numbers of odd-numbered and even-numbered picture elements, respectively, that have a zero intensity level. Memory address #1 in memories 56 and 58 will likewise contain the odd-numbered and even-numbered picture elements, respectively, having gray levels of value 1. By adding the contents of corresponding locations in memory units 56 and 58, a total histogram can be obtained by the microprocessor 52. Then, a threshold calculation can proceed, as indicated in FIG. 6a, which is a flowchart of the operations performed on the data obtained from memory units 56 and 58.

Figure 6A:
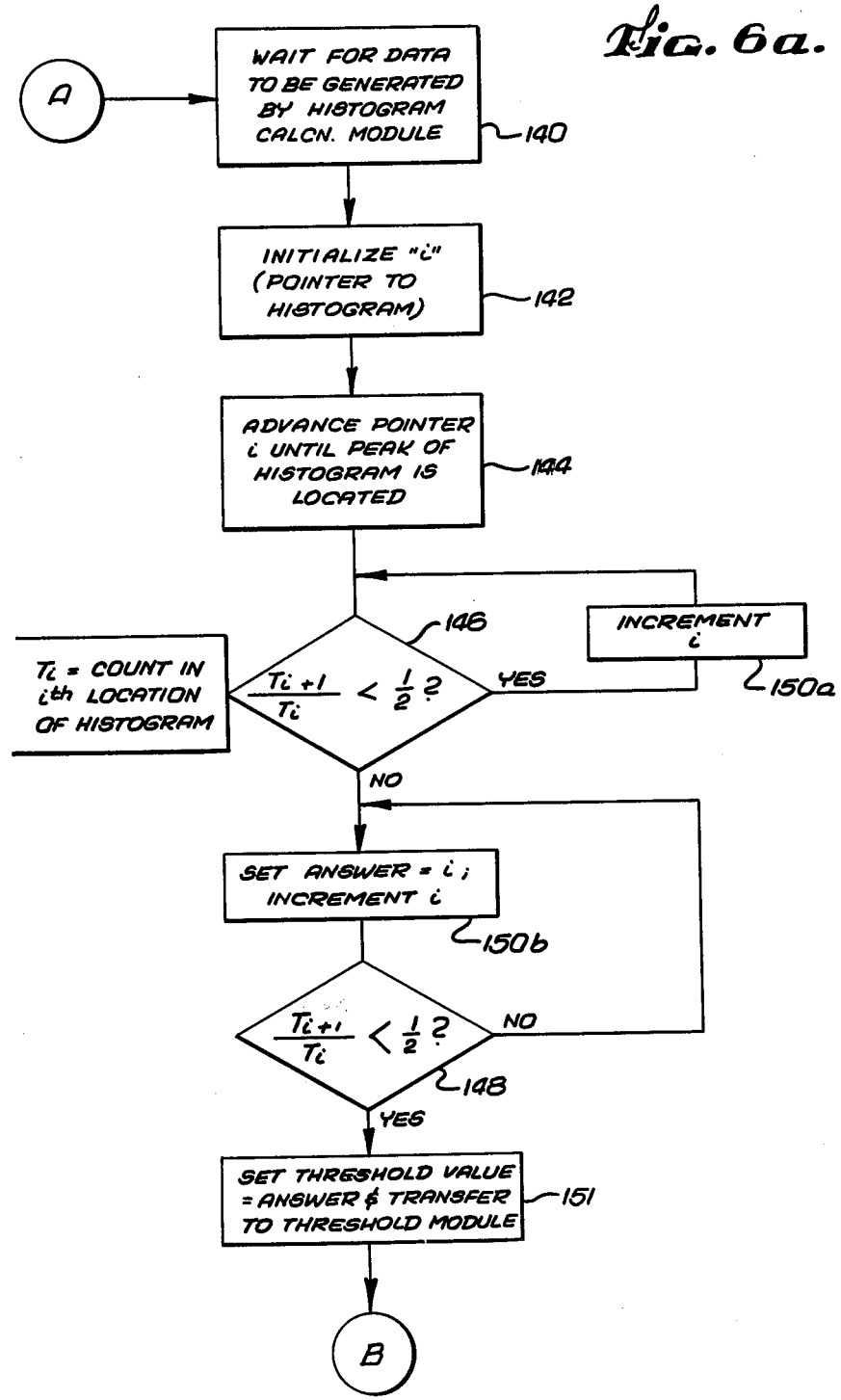
FIG. 6a is a functional flow chart of the threshold calcution module of FIG. 1.

As shown in FIG. 6a, the microprocessor will first wait for data to be generated by the histogram calculation module, as shown at 140. Then, a pointer to the histogram data, indicated as subscript i, is initialized, as shown in block 142. Next, in block 144, the pointer is advanced until the peak of the histogram is located. Since the shape of the histogram is generally the same as that shown in FIG. 2, a time saving can be effected by avoiding extensive analysis on that part of the histogram to the left side of the peak. Blocks 146, 148 and 150 illustrate how the threshold level is computed in accordance with this aspect of the invention. In block 146 the histogram count immediately following the currently indexed count, indicated as $T_{i+1}$, is divided by the currently indexed count $T_i$, and the ratio thereby obtained is compared with the ratio of one-half. If the ratio is less than one-half, the pointer i is incremented, as shown in block 150a, and the computation in block 146 is repeated. If the ratio is greater than one-half, the pointer i is also incremented, as shown in block 150b, and a new ratio of $T_{i+1}$ to $T_i$ is computed as shown in block 148. This new ratio is also compared with one-half, and if it is greater than one-half a return is made to block 150b, where the pointer i is incremented, and thence again to block 148. If the new ratio as determined in block 148 is less than one-half, the prior index value (i−1) is designated the threshold value, and this is transmitted to the image thresholding module, as shown in block 151.

A count ratio of greater than one-half as determined in block 146 is indicative of a flattening of the histogram curve. The second ratio test in block 148 determines when the histogram distribution curve drops again from its relatively flat region, as indicated by the position of the threshold line 50 in FIG. 2.

Image Thresholding Module

Figure 5:
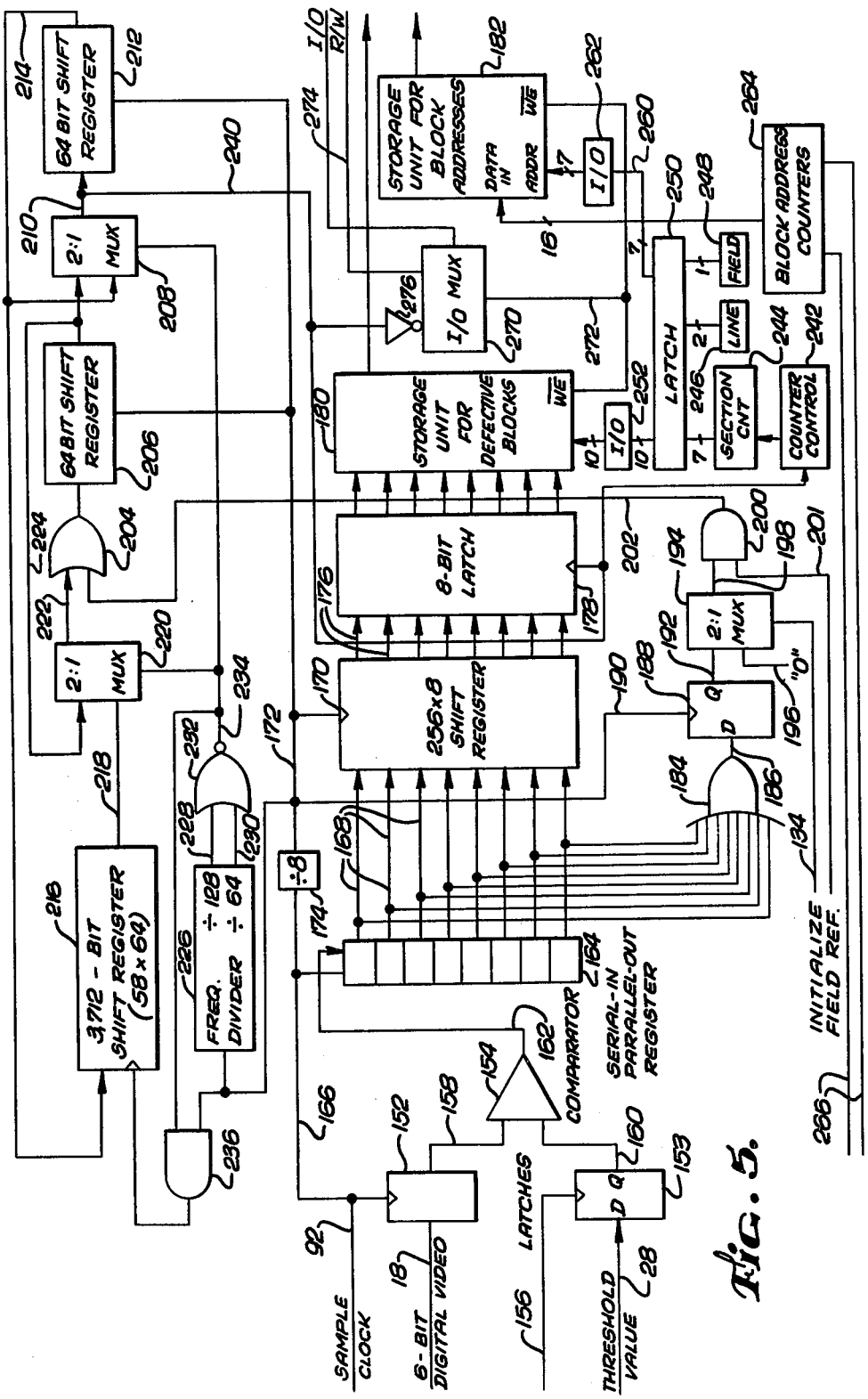
FIG. 5 is a schematic diagram of the image thresholding module of FIG. 1.

The next step is performed by hard-wired circuitry contained within the image thresholding module 22 (FIG. 1), illustrated in detail in FIG. 5. As shown, this module includes two six-bit latches 152 and 153 and a comparator 154. The six-bit digital video signal on line 18 is input to the latch 152 under control of the sample clock signal on line 92, and the threshold value is supplied over line 28 from the threshold calculation module 26 (FIG. 1) and is stored in latch 152, by an appropriate clocking signal on line 156. Outputs from the latches 152 and 153, on lines 158 and 160, respectively, are transmitted as inputs to the comparator 154, which provides a single-bit output signal on line 162, indicative of whether the six-bit video signal stored in latches 152 is greater than or less than the threshold value stored in latches 153. A logical "one" signal on line 162 indicates that the sampled video signal is greater than or equal to the threshold value, while a "zero" signal indicates that the video signal is less than the threshold value. Line 162 conveys this single-bit data stream to a serial-in-parallel-out shift register 164, which is clocked by a signal applied over line 166, also derived from the sample-rate clock signal on line 92.

The register 164 is eight-bits long and produces outputs on eight parallel output lines 168, connected as inputs to a shift register 170 having 256 successive positions, each eight-bits wide. The shift register 170 is clocked by a clocking signal on line 172 derived from the original sample clock signal, the frequency of which is divided by eight in a frequency divider 174. Thus, the picture elements clocked into the shift register 164 are divided into eight-bit bytes and then clocked successively into shift register 170. The shift register 170 has eight corresponding output lines 176 for transmitting outputs to an eight-bit latch 178, the outputs of which are directed to data input terminals of a storage unit 180 for storing "defective" blocks of data. A "block" of data is defined as an eight-by-eight-bit block, and as will be apparent, "defective" blocks are defined as those containing at least one logical "one" bit, indicative of an anomalous picture element. The ones in the data stream, it will be remembered, are indicative of surface anomalies in the part being examined, and these may be subsequently determined to constitute a rejectable defect.

To avoid having to store the entire frame of picture elements for analysis, the logic to be described with reference to FIG. 5 stores only those "defective" blocks of data containing indications of anomalous defects. A second storage unit 182 is used for storing coordinates or addresses of the defective blocks. The remaining logic in FIG. 5 arranges for the detection of ones in the data stream, and for appropriate clocking of the latch 178 and addressing of the storage units 180 and 182 to store only the defective blocks.

The FIG. 5 logic is complicated somewhat by the fact that conventional interlacing is used in the video scanning technique employed in the invention. Accordingly, the video data stream first provides picture elements of the odd field, and then picture elements of the even field. In particular, it will be observed as the description proceeds that shift-register storage is provided for an entire field of data.

Continuing now with the detailed description of the FIG. 5 circuitry, it will be seen that the eight output lines 168 from the serial-in-parallel-out register 164 are also connected as inputs to an OR gate 184, the output of which, on line 186 is transmitted as an input to a one-bit-latch 188. A clock signal for the latch is derived over line 190 from the frequency divider 174, and thus a one is stored in the latch 188 whenever a one appears on any of the output lines 168. The latch output on line 192 is provided as one input to a two-to-one multiplexer 194, the other input of which is a permanently wired zero, as indicated at 196. The zero is transmitted through the multiplexer 194 only when an initialize signal is present on control line 134 connected to the control input of the multiplexer 194. The output of the multiplexer 194 on line 198 is provided as one input to an AND gate 200, the other input of which is a field reference signal on line 201. When the odd field is being processed, the field reference signal as a logical "one", and enables the AND gate 200 to transmit the input signal on line 198 through the AND gate to its output line 202. When the even field is being processed, the AND gate 200 blocks transmission of an output signal.

The output signal on line 202 is connected as one input to an OR gate 204, the output of which is provided to a 64-bit shift register 206 and thence to one input of a multiplexer 208. The output of the multiplexer 208, on line 210 is input to another 64-bit shift register 212, the output of which is fed back over line 214 and provided as a second input to multiplexer 208 and as an input to yet another shift register 216, this one having 3,712 stages. The output of this shift register 216 is provided on line 218 as one input to another multiplexer 220, the output of which, on line 222, is connected as a second input to the OR gate 204. The output of the first 64-bit shift register on line 206, in addition to being supplied to the multiplexer 208, is fed back over line 224 as a second input to multiplexer 220.

Before turning to a description of the sequence of operations of the aforedescribed circuitry, the clock signals by means of which the various shift registers are controlled will first be briefly explained. The clock signal obtained from the frequency divider 174 is applied to yet another frequency divider 226, which divides the signal further by a factor of 128, the corresponding output being provided on line 228, and by a factor of 64, the corresponding output being provided on line 230. Lines 228 and 230 are applied as inputs to a NOR gate 232, the output of which, on line 234, is used to control the multiplexers 220 and 208. The NOR gate output on line 234 is also applied as an input to an AND gate 236, the other input of which is derived directly from the first frequency divider 174. The output of AND gate 236 is used to clock the 3,712-shift register 216.

Note, the 256×8 shift register 170 represents four lines of data from an input frame, since there are 512 picture elements in each line, and these are divided into eight-bit bytes. Thus, there are 64 such bytes in each line, and 256 such bytes in the four lines. Four lines, of course, represent one field of an eight line segment of data. Accordingly, the outputs of shift register 170, on line 176, are exactly four data lines behind, in a timing sense, the inputs on lines 168. The single-bit data stream applied to OR gate 204 on line 202 indicates whether there are "ones" in the data stream. A "one" in the data stream on line 202 indicates an eight-bit byte with at least one "one" in it being input over lines 168. Thus, the first 64-bit shift register 206 represents 64 bytes of data, or one complete line of information, there being a bit in the register for each byte of information in the line.

The clock signal applied to multiplexer 220 is timed such that the 64-bit register 206 is fed back over line 224 four times, representing four lines of data, and the OR gate 204 merges the present contents of the shift register 206 with the incoming data stream on line 202. Thus, after four cycles of the register 206 it contains a "one" if a "one" appeared in any of the four lines corresponding to that byte position. In effect, then, the 64-bit shift register 206 is representative of an 8×4 block of data, after the register has been cycled four times. After the four cycles, the contents of shift register 206 are transmitted through multiplexer 208 to the second 64-bit shift register 212, and are then cycled through this shift register four times. The data stream input to the second shift register 212, over line 210, is also transmitted over line 240 to the clocking terminal of the eight-bit latches 178, and to a counter control unit 242, the purpose of which will shortly be explained.

In the time that it takes for the first 64-bit shift register 206 to generate an output stream on line 210, four lines of data have been processed. Consequently, the data appearing on lines 176 from the 256×8 shift register 170 corresponds in time with the stream appearing on line 210, which can therefore be used to clock the eight-bit latch 178 whenever a "one" appears in the data stream.

Recall that the output of the second 64-bit shift register 212 is also transmitted back as an output to the large 3,712 bit shift register 216. This register has a capacity of 58 times 64 bits, i.e., it can store 58 bit vectors each representative of four lines of data. Thus, the shift register 216, together with the two 64-bit shift registers 206 and 212, represent a total of sixty 64-bit vectors, or a total of 240 lines, which is the number of lines in a complete field of video information. Because of this relationship, the registers 206, 212 and 216 function to store an entire field of information with respect to the content of each byte in the field. When it is time to scan the even field, the AND gate 200 prevents the transmission of new data over line 202 to the OR gate 204, but the bit vectors corresponding to the odd field are transmitted over input line 222 to the OR gate 204. In this manner, once "ones" have been detected in the odd field of the data stream, the corresponding picture elements in the even field will also be stored in the storage unit 180.

Appropriate address signals are generated for the storage unit 180 by the control counter 242, which is operative to increment a seven-bit section counter 244, this being a count of the defective blocks. The section counter in conjunction with a line counter 246, which is continually clocked from zero through three and back to zero again, and a field counter 248, which is clocked cyclically between zero and one, together generate a ten-bit address for the storage unit 180. The address is stored in a latch 250 and applied through an I-O control unit 252 to the address terminals of the storage unit 180. The seven-bit field corresponding to the section counter 244 is transmitted from the latch 250 over line 260 to a second I-O unit 262, through which the address is provided to the storage unit 182 for the block addresses of the stored information. The storage unit 180 will have stored in it a sequence of 8×8 blocks, these being the blocks containing at least one logical "one" picture element.

As discussed, storage block 182 is used to store block addresses, and these may be conveniently generated in a block address counter 264 provided with appropriate clocking signals over lines 266. The block addresses generated by the counters 264 indicate the horizontal and vertical coordinate positions of each defective block. Enabling the two storage blocks 180 and 182 for writing operations is controlled through an I/O multiplexer 270, the output of which on line 272 is applied to the inverse write-enable terminals of the storage units. The multiplexer 270 has two input lines, one being a read/write line 274 from the controlling microprocessor, and the other being provided through an inverter 276 from the data steam on line 240 from the multiplexer 208. When the control line 274 is in the "write" condition, the I/O multiplexer 270 selects input from the inverter 276, and the storage units 180 and 182 are enabled to write data when a "one" appears on the data stream line 240. If the control line 274 is in the "read" condition, the write-enable of signals are derived from an I-O control line 278, also provided by the controlling microprocessor. The effect of the logic described in relation to FIG. 5 is to store all the defective blocks in storage unit 180 and to store the block addresses in storage unit 182. By appropriate control signals from the microprocessor, these storage units can be accessed to obtain the defective block data and defective block addresses.

Region Growing and Statistics Updating

Figure 6B:
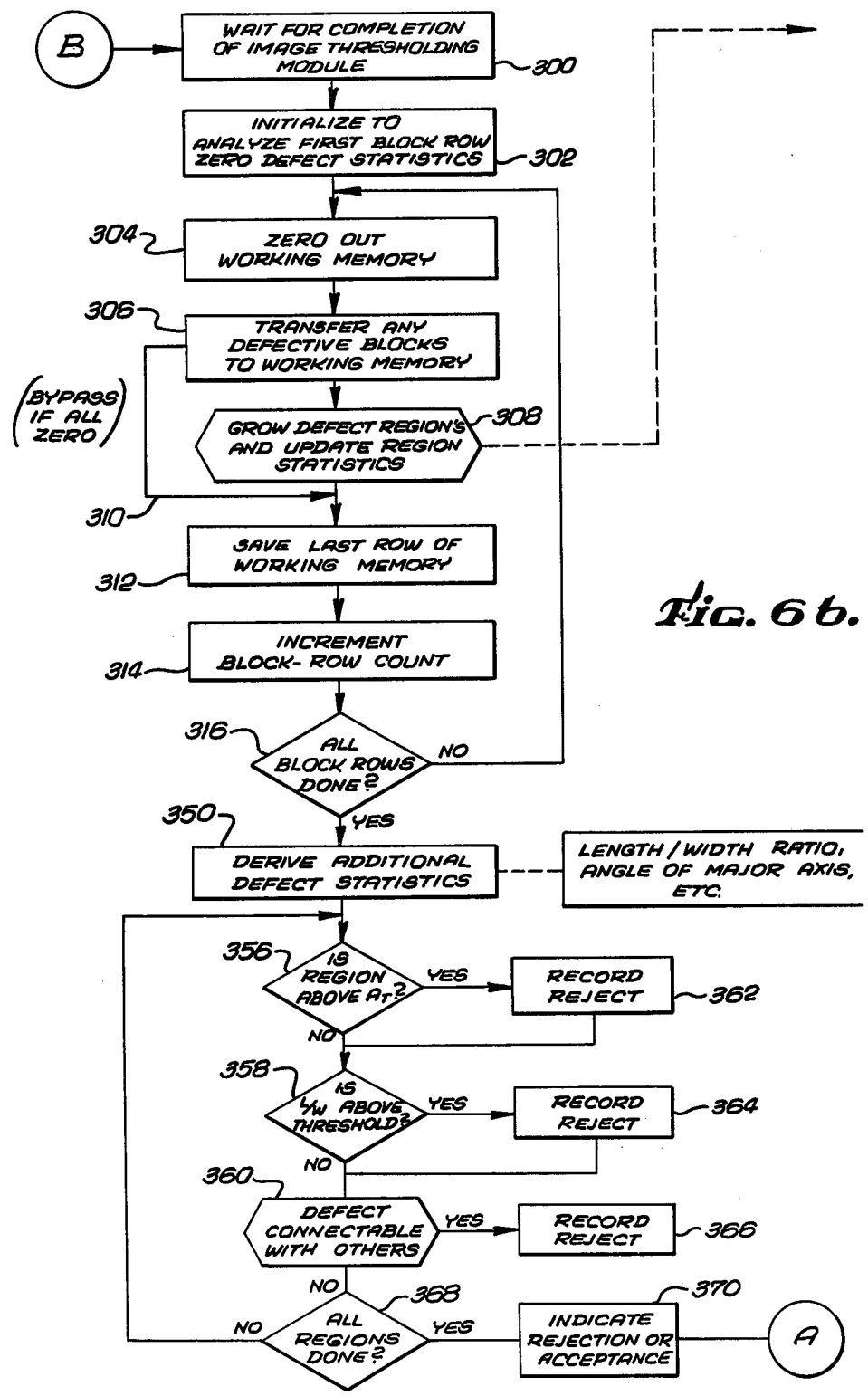
FIG. 6b is a functional flow chart of the region growing module and other defect analysis modules of FIG. 1.
Figure 7:
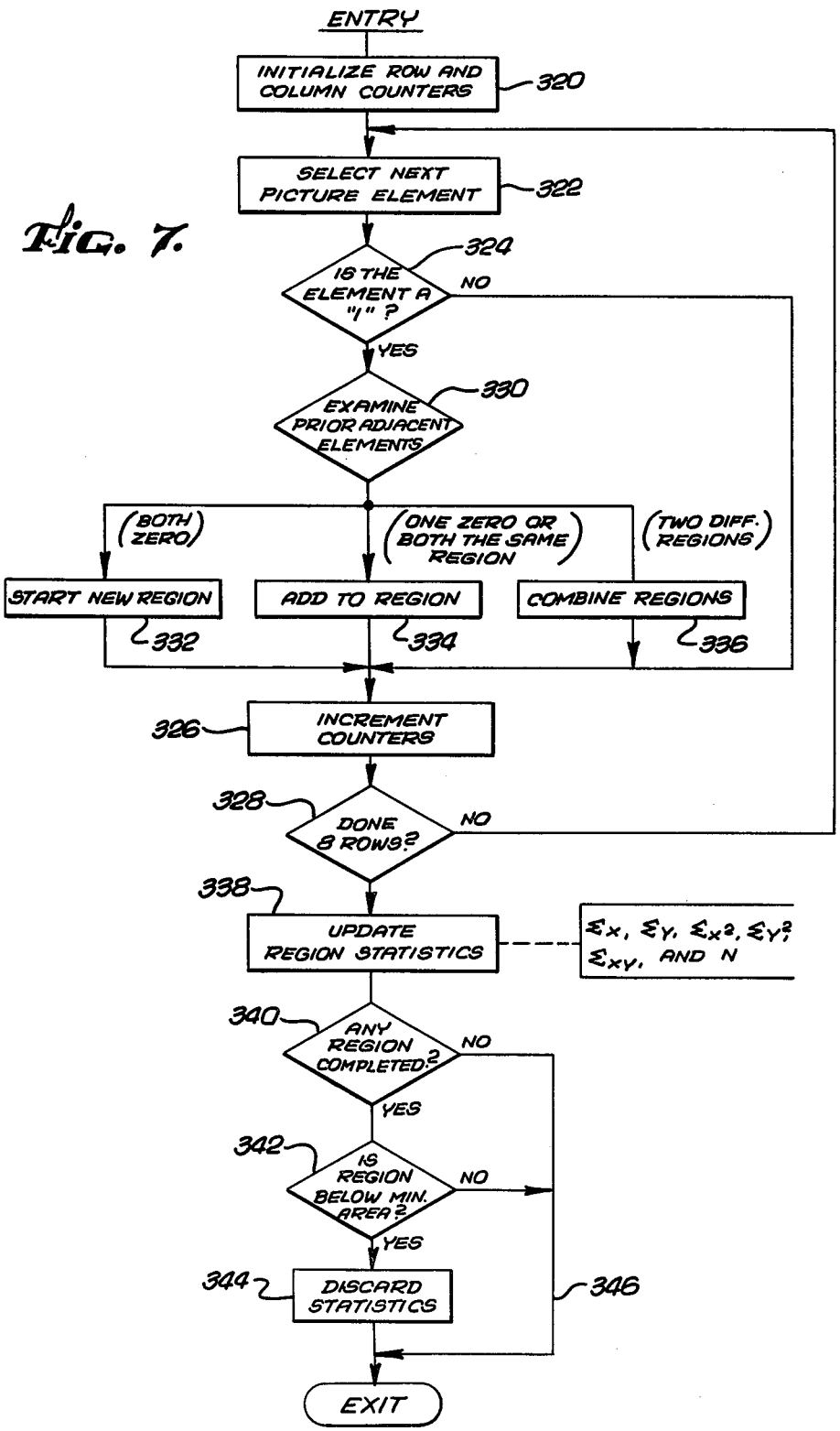
FIG. 7 is a functional flowchart of a region growing and statistic updating module shown in FIG. 6b.
Figure 8:
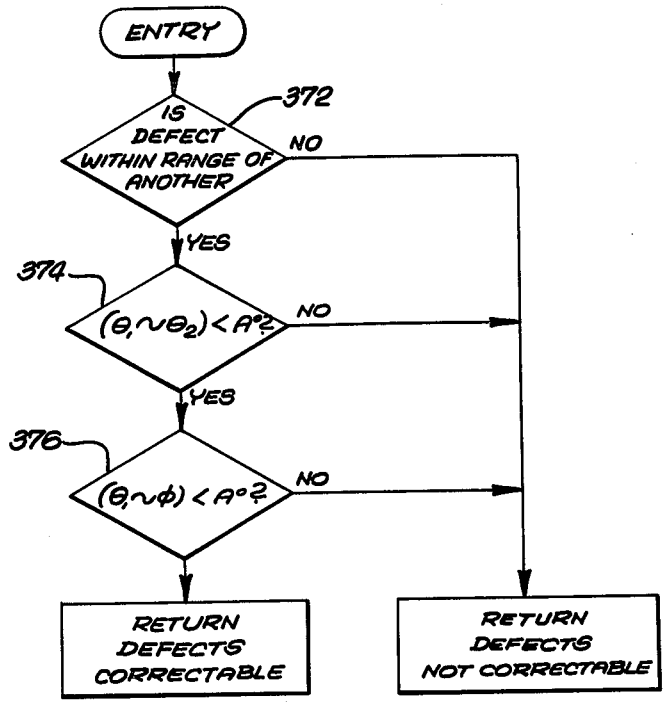
FIG. 8 is a functional flowchart showing more detail of a connectivity analysis module of FIG. 1.

Basically, the microprocessor logic for continuing processing of this data is shown in FIGS. 6b, 7 and 8. As shown at block 300 in FIG. 6b, the microprocessor waits for completion of the operation of the image thresholding module after the threshold value has been transmitted to the image thresholding module in accordance with the flowchart shown in FIG. 6a. The next step, shown in block 302, is to initialize the hardware to prepare for analysis of the first block-row. A "block-row" is the first eight rows of data, or, stated another way, the first row of 64 blocks. Other initialization is also performed in block 302, including the initialization of tables of statistics maintained on possible defects.

Next, in block 304, a working memory (not shown) is cleared, and then, in block 306, any defective blocks in the block-row being examined are transferred to the working memory, to provide a complete image of the first block-row in the working memory. When this has been done, the defect regions are "grown," as indicated in block 308, and statistics on each defect region are updated. Details of the functions performed in block 308 are described in more detail in relation to FIG. 7. In conjunction with performing the function in block 306, if any block-row contains no defective blocks, the functions of block 308 may, of course, be bypassed, as indicated by the path shown at 310.

After the region growing and statistic updating functions in block 308, the last row of the working memory is saved for future use, as indicated at block 312. This is necessary because part of the region growing function is to determine the extent of each continuous area of "ones" in the image. Consequently, it is necessary to preserve the last row of data in order to make comparisons with the first row of the next block row in the region growing process. After saving the last row, a block-row count is incremented, as indicated at 314, and the question is asked, in block 316, whether all the block-rows have been analyzed. If not, control is transferred back to block 304 to perform analysis on the next block-row. If all the block rows have been analyzed, the next step is to derive additional defect statistics with respect to each possible defect region, and to determine whether the defect statistics meet any of the predetermined criteria for rejectable defects. However, before these criteria can be meaningfully discussed, it will be helpful if the details of region growing and statistics updating are explained, with reference to FIG. 7.

The region growing and statistics updating functions begin with the initialization of row and column counters in a block-row, as indicated at block 320. Next a single picture element is selected for analysis, as indicated at block 322. Initially, of course, the picture element selected is the first element in the first row of the block row. The question is asked in block 324 whether the element is a "one." If it is a zero, control is transferred directly to block 326, where column and row counters are incremented, and then to block 328, where a determination is made as to whether all eight rows in the block row have been analyzed. If, however, the element under examination is a "one," the next question asked, in block 330, pertains to the condition of prior adjacent picture elements, i.e., the picture elements immediately above and immediately to the left of the one under examination. If both such prior adjacent elements are zero, the element under examination represents the first element in a new region. Accordingly, a new region will be started, indicated in block 332, a new statistical table set up, and the table initialized with the statistics relative to the first picture element of the region.

If, however, only one of the prior adjacent elements is zero, or if both are "one" and of the same region, then the new picture element under examination is one that should be added to the region to which one or both of the prior adjacent elements belong. This is indicated in block 334. Finally, if the two prior adjacent elements are designated as belonging to two different regions, then the situation is one in which two regions that were previously thought to be separate are in reality a single continuous region, and they must therefore be combined as indicated in block 336. This involves defining the smaller area of the two regions to belong to the same region as the larger one. After performing one of the operations indicated in blocks 332, 334 and 336, control is transferred to block 326, where row and column counters are incremented, and thence to block 328 to determine whether all eight rows of the block-row have been analyzed. If all rows have not been analyzed, control is transferred to block 322 to select the next picture element for analysis.

If all eight rows have been analyzed, this completes the analysis of a block-row, and the region statistics can be completely updated, as indicated in block 338. Alternatively, region statistics may be accumulated on an element-by-element basis. The region statistics maintained for each region of contiguous "ones" in the picture are basically cumulative statistics with respect to the coordinate values of each picture element in the region. More specifically, if a picture element has coordinates x and y with respect to some fixed origin of reference, then the statistics maintained are the cumulative sum of all the x coordinates, the cumulative sum of all the y coordinates, the cumulative sum of the square of the x coordinates, the cumulative sum of the square of the y coordinates, the cumulative sum of the product of the x and y coordinates, and finally, a count of the number of picture elements in the region. After the statistics have been updated, the question is asked whether any region has been completed in the course of analysis of the current block-row, as indicated in block 340. If a region has been completed, as will be the case if no additional picture elements were added to it in the last row of the block-row, then a further question is asked, as indicated in block 342, whether the completed region is below some minimum designated area. If it is, the statistics of the region are discarded, as indicated in block 344, it having been determined that regions below a certain size are of no significance for purposes of defect analysis. If no region has been completed, or if any completed region is above the minimum selected area, then the statistics are not discarded and the function of block 344 is bypassed, as indicated at 346. This completes the region growing and basic statistics updating functions of block 308 in FIG. 6b, and control is then transferred back to the functions in FIG. 6b as previously described.

After the block-rows have all been analyzed, as determined in block 316 of FIG. 6b, additional defect statistics are derived as indicated in block 35. These include the determination of an ellipse of equivalent area to the defect, having dimensions of length (l) and width (w), and the calculation of a length-to-width ratio (l/w), which typically has significance in a determination of the nature of the defect. The length-to-width ratio is calculated from the primary accumulated statistics in accordance with the following equation:

$$\frac{1}{w} = \frac{(\Sigma x^2/N)\cos^2\theta + (\Sigma xy/N)\sin 2\theta + (\Sigma y^2/N)\sin^2\theta}{(\Sigma y^2/N)\cos^2\theta - (\Sigma xy/N)\sin 2\theta + (\Sigma x^2/N)\sin^2\theta},$$

or the reciprocal of this expression; where:
$\Sigma x^2$ = sum of squares of x coordinates,
$\Sigma y^2$ = sum of squares of y coordinates,
$\Sigma xy$ = sum of products of x and y coordinates,
N = total number of picture elements in the region,
$\theta$ = angle of major axis of x axis, given by the following equation:
$\theta = -\frac{1}{2}(\tan^{-1}((2\Sigma xy/N)/((\Sigma x^2/N)-(\Sigma y^2/N))))$.

By convention, 1/w is to be greater than or equal to unity, and the ratio is inverted if a value less than unity is obtained.

Individual Defect Analysis

After these additional defect statistics have been computed in block 350, various defect tests are applied, in blocks 356, 358, and 360. In block 356, the question is asked whether the area of the region is above some selected area threshold $A_T$. If so, the region constitutes a rejectable defect, and the rejection is recorded in the statistics, as indicated at block 362. The next test, in block 358, is to inquire whether the length-to-width ratio is above a preselected threshold. If it is, again a rejectable defect exists, and record of this fact is made as indicated in block 364. The final test, in block 360, is to determine whether each defect under examination is connectable with others, even though it may be below the threshold level of area and may have an acceptable length-to-width ratio. If the defect is connectable with others, in accordance with criteria to be further discussed, the reject is recorded as indicated in block 366. Finally, a determination is made in block 368 whether all regions have been analyzed in this manner. If not, control is transferred back to block 356 to perform the same test on the other regions. If all regions have been so analyzed, an indication is made as to whether the part is accepted or rejected, as indicated in block 370. After this, control is transferred through the connecting circles labeled A to block 140 in FIG. 6a, and the microprocessor has no other immediate function but to wait for futher data to be generated by the histogram calculation module, this data relating to a new frame of information.

Connectivity Analysis

In order to determine whether a defect is connectable with others, the steps illustrated in FIG. 8 are performed. First, the question is asked in block 372q whether the defect under study is within a preselected range of another neighboring defect. The preselected range may be defined as an absolute distance, or, preferably, may be defined as multiple of the length of the major axis of the defect. In any event, if the defect is not within the preselected range of a neighboring defect, the defect is not considered to be connectable with other defects. If the defect is within the preselected range, two tests are made with respect to its angular orientation. The first test, in block 374, is to determine whether the difference between the angular orientations of the two major axes is within a preselected angle, A. If not, the defects are not considered to be connectable. If the angular difference is within the range A, the major axes of the two defects are approximately parallel, but not necessarily collinear. The major axes of the defects may for example, be parallel but practically side by side, in which case it would be most unlikely that the defects represented surface portions of a continuous crack or fissure. Accordingly, another orientation test is made, as shown in block 376, to determine whether the angle between the major axis of the defect under consideration and the line joining the centers of mass of the two defects is within the anglar limit A.

Figure 9A:
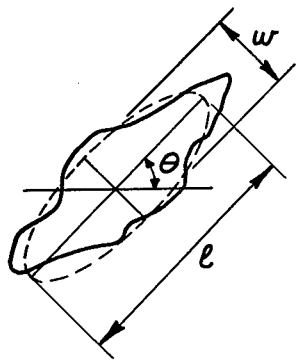
FIG. 9a is a diagrammatic view of a defect region with an ellipse of equal area drawn around the region.
Figure 9B:
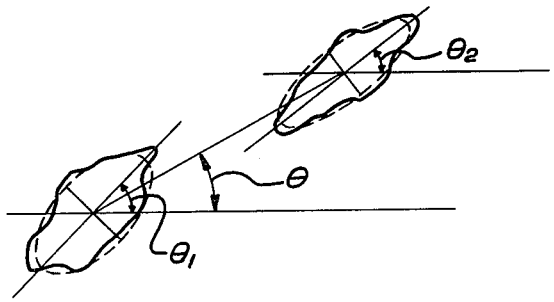
FIG. 9b is a diagrammatic view of a pair of adjacent defect regions showing their angular orientations as considered in the connectivity analysis module.

As can be seen from FIG. 9b, if this difference in angle is less than the prescribed maximum A, then the two defects are not only nearly parallel, are nearly collinear as well, and may well represent the surface portions of a continuous defect that extends beneath the surface for a portion of its length. Accordingly, if the test performed in blocks 372, 374, and 376 all result in affirmative answers, a return is made to block 360 in FIG. 6b with the indication that a rejectable defect exists.

Other criteria for rejectable defects may be devised. For example, it may be advisable to require collinearity of three regions for rejectability. It will be appreciated that the specific criteria employed depend to a great extent on the nature and geometry of the parts being examined. In any event, the specific criteria and tests for rejection described in this specification are intended to be illustrative only and the invention in its broadest sense is not intended to be limited to these specific tests. The present invention represents a significant advance in the field of automated detection of defects in manufactured parts, and in particular, the invention provides for the detection of defects without operator intervention, and based upon predefined rejection criteria. Various modifications may be made to the illustrative embodiment without departing from the spirit and scope of the invention. Accordingly, the invention is not to be limited except as by the appended claims.

We claim:
1. A defect analysis system for examining a part to determine whether defects are present, said system comprising:
first means for obtaining electrical signals representative of the condition of a plurality of discrete picture elements in a field of view of the part presented for analysis;
thresholding means coupled to said first means for generating a set of electrical signals indicative of picture elements of an anomalous type distinct from the other picture elements;
region growing means for associating contiguous picture elements of the anomalous type to define multiple regions of anomalous picture elements in a single raster scan of the field of view being analyzed;
region statistics generation means for generating statistics relative to the size, shape and orientation of the anomalous regions during the same single raster scan; and
region analysis means for comparing the region statistics with predetermined rejection parameters to determine whether a rejectable defect exists in the part.

2. A defect analysis system as set forth in claim 1, wherein:

said region statistics generation means includes means for recording the position, area, length-to-width ratio and orientation of each region.

3. A defect analysis system as set forth in claim 2, wherein said region analysis means includes:
means for comparing the area of a region with a first preselected limit wherein regions smaller in area than the first preselected limit are disregarded; and
means for comparing the area of a region with a second preselected minimum area, wherein regions larger than the second preselected minimum area are designated as rejectable defects.

4. A defect analysis system as set forth in claim 2, wherein said region analysis means includes:
means for comparing the length-to-width ratio of a region with a preselected threshold ratio, wherein regions having a length-to-width ratio higher than the threshold ratio are designated as rejectable defects.

5. A defect analysis system as set forth in claim 2, wherein said region analysis means includes:
means for comparing the spacing between and orientation of two regions with respective preselected spacing and orientation parameters to determine whether two regions together constitute a rejectable defect.

6. A defect analysis system as set forth in claim 5, wherein said means for comparing include:
means for determining the centers of mass of the two regions;
means for comparing the distance between the centers of mass of the two regions, with a preselected multiple of the length of one of the regions;
means for comparing the difference in angular orientations of the regions with a preselected angle; and
means for comparing the difference between the angular orientation of one region and the angular orientation of a line joining the centers of mass of both regions, with a preselected angle, wherein a rejectable defect occurs when the necessary distance and angle values are smaller than the corresponding preselected values.

7. A defect analysis system as set forth in claim 1, wherein:
said system further includes a source of radiation directed to the part being examined;
the condition of the picture elements that renders anomalous elements distinct is the intensity of radiation reflected from each element; and
said thresholding means includes
histogram calculation means for accumulating counts of picture elements for corresponding levels of radiation intensity,
means for determining from the accumulated counts a threshold level of intensity above which a picture element will be considered to be anomalous, and
image transformation means for comparing each picture element with the threshold level and thereby generating a binary image of the field of view.

8. A deflect analysis system as set forth in claim 7, wherein said histogram calculation means and said image transformation means are implemented in hard-wired form to increase the speed of operation.

9. A surface defect analysis system for examining a part to determine whether structural defects are present, said system comprising:
a source of light directed to the part being examined;
video camera means for obtaining analog electrical signals representative of the intensity of light emitted by discrete picture elements in an image frame of the part presented for analysis;
thresholding means coupled to said video camera means, for generating binary electrical signals indicative of anomalous picture elements having light intensities substantially different from the other picture elements;
region growing means for associating contiguous anomalous picture elements to define multiple regions of anomalous picture elements in a single raster scan of the image frame presented for analysis;
region statistics generation means for generating statistics relative to the size, shape and orientation of the anomalous regions during the same single raster scan; and
region analysis means for comparing the region statistics with predetermined rejection parameters, to determine whether a rejectable defect is present in the part.

10. A surface defect analysis system as set forth in claim 9, wherein:
said region statistics generation means includes means for recording the position, area, length-to-width ratio and orientation of each region.

11. A surface defect analysis system as set forth in claim 10, wherein said region analysis means includes:
means for comparing the area of a region with a first preselected limit, wherein regions smaller in area than the first preselected limit are disregarded; and
means for comparing the area of a region with a second preselected limit wherein regions larger in area than the second preselected limit are designated as rejectable defects.

12. A surface defect analysis system as set forth in claim 10, wherein said region analysis means includes:
means for comparing the length-to-width ratio of a region with a preselected threshold ratio, wherein regions having a length-to-width ratio higher than the threshold ratio are designated as rejectable defects.

13. A surface defect analysis system as set forth in claim 10, wherein said region analysis means includes:
means for comparing the spacing between and orientation of two regions with respective preselected spacing and orientation parameters to determine whether two regions together constitute a rejectable defect.

14. A surface defect analysis system as set forth in claim 13, wherein said means for comparing include:
means for comparing the distance between the centers of mass of the two regions, with a preselected multiple of the length of one of the regions;
means for comparing the difference in angular orientations of the regions with a preselected angle;
means for comparing the difference between the angular orientation of one region and the angular orientation of a line joining the centers of mass of both regions, within a preselected angle, wherein a rejectable defect occurs when the necessary distance and angle values are smaller than the corresponding preselected values.

15. A surface defect analysis system as set forth in claim 9, wherein said thresholding means includes histogram calculation means for accumulating counts of picture elements for corresponding levels of light intensity, means for determining from the accumulated counts a threshold level of intensity above which a picture element will be considered to be anomalous, and image transformation means for comparing each picture element with the threshold level and thereby generating a binary frame image.

16. A surface defect analysis system as set forth in claim 15, wherein said histogram calculation means and said image transformation means are implemented in hard-wired form to increase the speed of operation.

17. A surface defect analysis system as set forth in claim 15, wherein said means for determining a threshold level includes:

means for comparing the ratio of two adjacent histogram values with a preselected ratio; and means for designating a histogram value the threshold level based on the results obtained from two successive comparison operations by said means for comparing.

18. A surface defect analysis system as set forth in claim 17, wherein said preselected ratio is 0.5.

19. A method for detection of defects in a manufactured part, comprising the steps of:

obtaining electrical signals representative of a plurality of picture elements in a field of view of a part presented for inspection;

transforming these signals into a set of binary electrical signals indicative of anomalous picture elements that are optically distinct from other picture elements;

associating contiguous anomalous picture elements to define multiple regions of anomalous picture elements in a single raster scan of the field of view presented for inspection;

generating statistics relative to physical characteristics of each region during the same single raster scan; and comparing region statistics with predetermined rejection parameters to determine whether a rejectable defect is present.

20. A method as set forth in claim 19, wherein said step of transforming the signals includes:

generating a histogram of the entire image frame to define the relationship between light intensity and numbers of picture elements;

calculating an optimum threshold level from the histogram; and generating a binary frame image by comparing each picture element intensity with the threshold level.

21. A method as set forth in claim 19, wherein:

said step of generating statistics includes recording the size, position, length-to-width ratio, and angular orientation of each region.

22. A method as set forth in claim 21, wherein:

said step of comparing region statistics with predetermined rejection parameters includes, comparing the area of each region with a preselected limit above which the region will be designated a defect.

23. A method as set forth in claim 21, wherein:

said step of comparing region statistics with predetermined rejection parameters includes comparing the length-to-width ratio of each region with a preselected value, above which the region will be designated a defect.

24. A method as set forth in claim 21, wherein said step of comparing region statistics with predetermined rejection parameters includes:

comparing the distance to each neighboring region with a preselected relative distance; and comparing the angular orientation of each region with that of each neighboring region, whereby a rejectable defect will be found if two regions are relatively close together and are substantially collinear.

* * * * *